US00PP34308P2

(12) United States Plant Patent
Kamstra

(10) Patent No.: US PP34,308 P2
(45) Date of Patent: Jun. 7, 2022

(54) ***IBERIS* PLANT NAMED 'IBSZ0007'**

(50) Latin Name: ***Iberis* x *hybrida***
Varietal Denomination: IBSZ0007

(71) Applicant: SYNGENTA CROP PROTECTION AG, Basel (CH)

(72) Inventor: Silvan Adelmar Kamstra, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/370,135

(22) Filed: Jul. 8, 2021

(51) Int. Cl.
*A01H 5/02* (2018.01)
*A01H 6/20* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Dale Skalla

(57) ABSTRACT

A new *Iberis* plant named 'IBSZ0007' particularly distinguished by its very large pure lavender flowers that are long flowering, grass green foliage and an upright plant habit.

1 Drawing Sheet

Latin name of the genus and species of the plant claimed: *Iberis* x *hybrida.*

Varietal denomination: 'IBSZ0007'.

BACKGROUND OF THE NEW PLANT

The present invention comprises a new *Iberis*, botanically known as *Iberis* x *hybrida,* and hereinafter referred to by the variety name 'IBSZ0007'.

'IBSZ0007' is a product of a planned breeding program derived from embryo rescue of a interspecific cross. The new cultivar 'IBSZ0007' has very large lavender flowers, grass green foliage, and an upright plant habit.

'IBSZ0007' originates from an interspecific cross made by embryo rescue in The Netherlands in 2014. The female parent was an unpatented, proprietary plant designated 'S0473-52V' with large lavender flowers flowers, darker green foliage. It belongs to the species I. *umbelleta.*

The male parent of 'IBSZ0007' is an unpatented, proprietary plant designated 'P1369V', belonging to the species I. *sempervirens*. It has large white flowers and a compact habit.

'IBSZ0007' was selected as one flowering plant within the progeny of the stated cross in April 2015 in a greenhouse in Enkhuizen, The Netherlands.

The first act of asexual reproduction of 'IBSZ0007' was accomplished when vegetative cuttings were propagated from the initial selection in June 2015 in a greenhouse in Enkhuizen, The Netherlands.

BRIEF SUMMARY OF INVENTION

Horticultural examination of plants grown from cuttings of the plant initiated in June 2015 in Enkhuizen, The Netherlands, and continuing thereafter, has demonstrated that the combination of characteristics as herein disclosed for 'IBSZ0007' are firmly fixed and are retained through successive generations of asexual reproduction.

'IBSZ0007' has not been observed under all possible environmental conditions. The phenotype may vary significantly with variations in environment such as temperature, light intensity and day length.

A Plant Breeder's Right for this cultivar has been applied for in the European Union on Jun. 25, 2021, No. 2021/1708. 'IBSZ0007' has not been made publicly available prior to the effective filing date of this application, notwithstanding any disclosure that may have been made less than one year prior to the effective filing date of this application by the inventor or another who obtained 'IBSZ0007' directly from the inventor.

The following traits have been repeatedly observed and are determined to be basic characteristics of the new variety. The combination of these characteristics distinguishes this *Iberis* as a new and distinct variety.

BRIEF DESCRIPTION OF THE PHOTOGRAPHS

The accompanying photographic drawings show typical flower and foliage characteristics of 'IBSZ0007' with colors being as true as possible with an illustration of this type.

Figure 1:
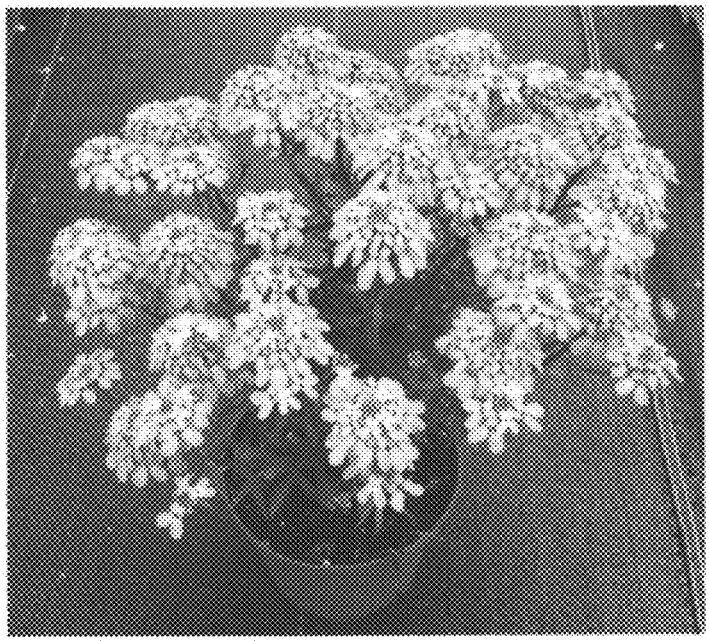
Figure 2:
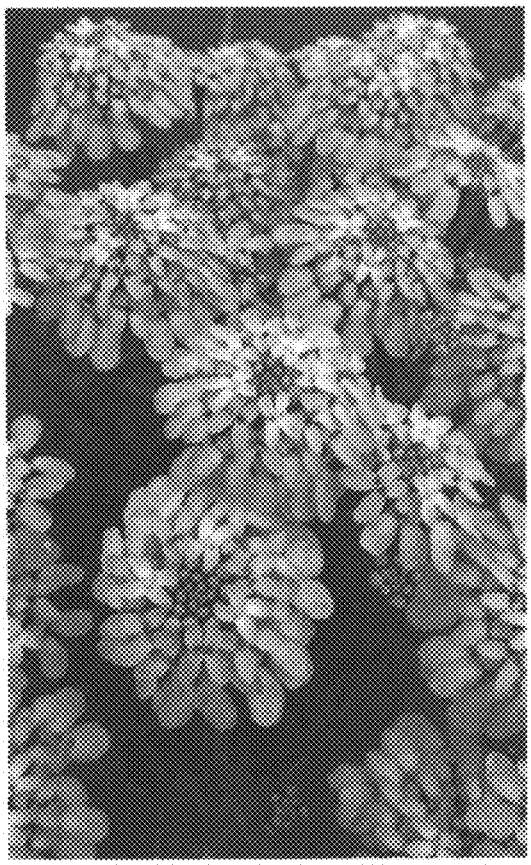

The photographic drawings show in FIG. 1 a flowering plant of the new variety and FIG. 2 shows a detailed flower close up.

DETAILED BOTANICAL DESCRIPTION

The plant descriptions and measurements were taken in Enkhuizen, The Netherlands under natural light in June 2021. These plants were approximately 10 weeks old and were grown in 13 cm pots in outside container field trials. The plants used for the photographs were about 10 weeks old growing in Enkhuizen, The Netherlands and the photographs were taken in June 2021.

Color Chart used: Royal Horticultural Society Colour Chart (RHS) 2001

TABLE 1

DIFFERENCES BETWEEN THE NEW VARIETY 'IBSZ0007' AND A SIMILAR VARIETY

| | 'IBSZ0007' | 'Masterpiece'(U.S. Plant Pat. No. 22,280) |
|---|---|---|
| Flower color: | Lavender | White |
| Plant size: | Larger 30 cm | 20-25 cm |
| Branching habit: | More branching | Less branching |

Plant:
- *Form, growth and habit.*—Upright mounded and branched.
- *Plant height.*—30-40 cm.
- *Plant height (inflorescence included).*—30 cm (without pot).
- *Plant width.*—25.0 cm.

Roots:
- *Number of days to initiate roots.*—About 8 days at about 18 degrees C.
- *Number of days to produce a rooted cutting.*—3.5 weeks at 18 degrees C.
- *Type.*—Fine, fibrous, white, moderate branched.
- *Color.*—RHS N155B but whiter.

Foliage:
- *Arrangement and attachment.*—Alternate simple, sessile.
- *Immature, leaf color, upper surface.*—RHS 141B.
- *Lower surface.*—RHS 141B.
- *Mature, leaf color, upper surface.*—RHS 141B.
- *Lower surface.*—RHS 141B.
- *Length.*—3-4 cm.
- *Width.*—0.4-0.6 cm.
- *Shape.*—Slightly oblanceolate.
- *Base shape.*—Attenuate, clasped to stem.
- *Apex shape.*—Rounded.
- *Margin.*—Slightly serrate.
- *Texture, upper surface.*—Glabrous.
- *Lower surface.*—Glabrous.
- *Color of veins, upper surface.*—RHS 141A.
- *Color of veins, lower surface.*—RHS 141A.
- *Venation pattern.*—Only main middle vein visible.
- *No petiole.*—Sessile.

Stem:
- *Quantity of main branches.*—About 20, with each 3-4 lateral branches.
- *Color of stem.*—RHS 141C.
- *Length of stem.*—20-25 cm (including peduncle).
- *Diameter.*—0.5 cm.
- *Length of internodes.*—0.5-1.5 cm.
- *Texture.*—Rough, no hairs.

Inflorescence:
- *Type.*—Short simple corymb.
- *Quantity of inflorescences per plant.*—More than 30.
- *Quantity of flowers per inflorescence.*—More than 50.
- *Inflorescence length.*—2-4 cm.
- *Inflorescence width.*—3.5-5 cm at widest point.
- *Lastingness of individual blooms. on the plant.*—About 14 days.
- *Fragrance.*—None.

Bud (just before opening/showing color):
- *Color.*—RHS 80B.
- *Length.*—0.4 cm.
- *Width.*—0.4 cm.
- *Shape.*—Globose.
- *Pedicel color.*—RHS 141B.
- *Pedicel length.*—0.4 cm.
- *Pedicel diameter.*—0.5 mm.
- *Pedicel texture.*—Smooth.

Corolla:
- *Shape of corolla.*—4 petals — 2 small and 2 large, smaller and bigger petals are opposite of each other.
- *Petal, length.*—0.5-1.5 cm.
- *Petal, width.*—0.4-0.8 cm.
- *Floret depth.*—1 cm.
- *Flower depth.*—3.5-4 cm.
- *Petal (all) color, upper surface.*—RHS 81C.
- *Lower surface.*—RHS 81C.
- *Upper/shorter petals.*—
- *Length.*—0.4-0.7 cm.
- *Width.*—0.5 cm.
- *Shape.*—Obovate.
- *Apex shape.*—Rounded.
- *Margin.*—Entire.
- *Lower/longer petals.*—
- *Length.*—1.0-1.5 cm.
- *Width.*—0.6-0.8 cm.
- *Shape.*—Obovate to truncate.
- *Apex shape.*—Rounded.
- *Margin.*—Entire.
- *Petal (all) texture, upper surface.*—Smooth.
- *Lower surface.*—Smooth.

Calyx:
- *Quantity.*—4 sepals.
- *Color, upper surface.*—RHS 141B.
- *Lower surface.*—RHS 141A.
- *Length.*—0.5 cm.
- *Width.*—0.3 cm.
- *Shape.*—Ovate.
- *Apex shape.*—Rounded.
- *Base.*—Fused.
- *Margins.*—Entire.
- *Texture, upper/inner surface.*—Smooth.
- *Lower/outer surface.*—Smooth.

Reproductive organs:
- *Gynoecium.*—
- *Pistil quantity.*—1.
- *Length.*—0.4-0.6 cm.
- *Style color.*—RHS 144B.
- *Style length.*—0.2 cm.
- *Stigma color.*—RHS 151C.
- *Stigma shape.*—Lobed.
- *Ovary.*—Not very discernable.
- *Androecium.*—
- *Stamens, quantity.*—6.
- *Color of filaments.*—RHS 145D.
- *Length of filaments.*—0.2-0.3 cm.
- *Anther color.*—RHS 151D.
- *Anther length.*—0.05 cm.
- *Anther shape.*—Oval.
- *Pollen amount.*—Some pollen.
- *Fertility/seedset.*—Neither seed nor fruit production has been observed.
- *Disease/pest resistance.*—Resistance to pathogens and pests common to *Iberis* has not been observed.
- *Drought tolerance and cold tolerance.*—Medium hardy perennial. Tolerates high temperature to at least 30 degrees C. Tolerates low temperatures to degrees minus 7 C. No specific drought tolerance has not been observed.

What is claimed is:

1. A new and distinct variety of *Iberis* plant named 'IBSZ0007' substantially as illustrated and described herein.

* * * * *